United States Patent [19]

Kaschig

[11] Patent Number: 4,997,964
[45] Date of Patent: Mar. 5, 1991

[54] IRIDIUM COMPLEXES AND THE USE THEREOF

[75] Inventor: Jürgen Kaschig, Freiburg, Fed. Rep. of Germany

[73] Assignee: Ciba-Geigy Corporation, Ardsley, N.Y.

[21] Appl. No.: 338,416

[22] Filed: Apr. 12, 1989

Related U.S. Application Data

[63] Continuation of Ser. No. 47,097, May 8, 1987, abandoned.

[30] Foreign Application Priority Data

May 16, 1986 [CH] Switzerland .................. 1988/86

[51] Int. Cl.$^5$ ............................................. C07F 15/00
[52] U.S. Cl. ................................................... 556/137
[58] Field of Search ........................................ 556/137

[56] References Cited

U.S. PATENT DOCUMENTS 4,290,961 9/1981 Mestroni et al. ................ 260/397.4

FOREIGN PATENT DOCUMENTS 3405611 8/1984 Fed. Rep. of Germany ...... 556/137

OTHER PUBLICATIONS

A. L. McCrary and W. L. Howard, *Chelating Agents*, vol. 5, p. 340, Kirk-Othmer, 3rd Ed.
Griffith, W. P. *The Chemistry of the Rare Platinum Metals (Os, Ru, Ir & Rh)*, 1967, Interscience, pp. 262, 263, 82–84, 86, 87, 109, 350, 351, 169, 172.
Hartley, F. R. *The Chemistry of Platinum & Palladium*, Wiley, 1973, See Index under Ethylenediamine Complexes.

*Primary Examiner*—Arthur C. Prescott
*Attorney, Agent, or Firm*—Stephen V. O'Brien

[57] ABSTRACT

Optically active iridium complex of the formula I

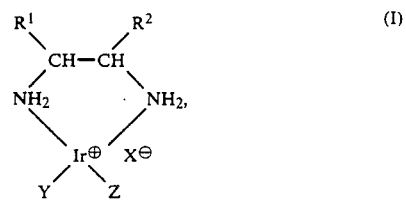

in which the >CH—CH< group contains at least one chiral C atom, $R^1$ and $R^2$ together are unsubstituted or $C_1$–$C_4$-alkyl substituted —$(CH_2)_4$— or $R^1$ is alkyl, unsubstituted or $C_1$–$C_4$-alkyl substituted, cycloalkyl, aryl, or aralkyl or alkaralkyl and $R^2$ is H, $X^-$ is the anion of a monobasic inorganic or organic acid, and Y and Z are each ethylene or Y and Z together are an acyclic or cyclic diene having 6 to 10 c atoms whose diene groups are bonded via 1 or 2 C atoms, are suitable for use as enantioselective homogeneous catalysts.

8 Claims, No Drawings

IRIDIUM COMPLEXES AND THE USE THEREOF

This application is a continuation of application Ser. No. 047,097 filed 5-8-87 now abandoned.

The invention relates to optically active cationic iridium(I) complexes with asymmetric 1,2-diamine ligands and a diene ligand, to the preparation thereof and to the use thereof as enantioselective catalysts.

G. Zassinovich et al., Journal of Organometallic Chemistry, 222, pp. 323-329 (1981), describes cationic iridium(I) complexes with a 1,5-cyclooctadiene ligand and a 2-pyridinalimine ligand which is substituted on the imine-N atom by optically active α-phenylethyl or 3-pinanemethyl. They act as enantioselective homogeneous catalysts in the transfer hydrogenation of prochiral ketones with isopropanol. It is true that the reaction gives high yields, but the optical yield (enantiomer excess) is relatively low.

Cationic iridium(I) complexes with a 1,5-cyclooctadiene ligand and a racemic 1,2-diphenylethylenediamine ligand are known from R. Urson et al, Inorganica Chimica Acta, 73 (1983), pp. 275-279. It is also mentioned that these iridium complexes are suitable to use as catalysts for the transfer hydrogenation of acetophenone and cyclohexene with ispropanol. The yields are relatively low and nothing is said about increase in the concentration of optical isomers.

It has been found that high yields and a high increase in the concentration of optical isomers can be obtained if the iridium complexes contain asymmetric diprimary 1,2-diamine ligands.

The invention provides optically active iridium complexes of the formula I

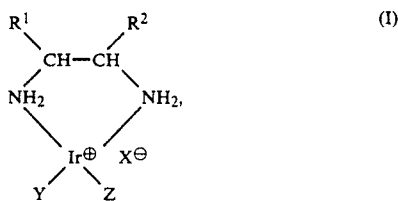

in which the >CH—CH< group contains at least one chiral C atom, $R^1$ and $R^2$ together are unsubstituted or $C_1$-$C_4$-alkylsubstituted —$(CH_2)_4$—, or $R_1$ is alkyl, unsubstituted or $C_1$-$C_4$-alkyl substituted, cycloalkyl, aryl or aralkyl or alkaralkyl and $R^2$ is H, X is the anion of a monobasic inorganic or organic acid, and Y and Z are each ethylene or Y and Z together are an open-chain or cyclodiene having 6 to 10 C atoms whose diene groups are bonded via 1 or 2 C atoms.

Optically active signifies that at least one chiral C atom is predominantly present in the S- or R-configuration.

An anion of a monobasic inorganic or organic acid can be for example $F^\ominus$, $CL^\ominus$, $BR^\ominus$, $I^\ominus$, $ClO_4^\ominus$, $NO_3^-$, $BrO_3$, $HSO_4$, $H_2PO_3$, $H_2PO_4$, $BF_4$, $PF_6$, $SbF_6$, $AsF_6$, $SbCl_6$, $SbCl_5F^\ominus$, $HCOO^\ominus$, $CH_3COO^\ominus$, $CF_3COO^\ominus$, $CH_3SO_3$, $CCl_3SO_3$, $CF_3SO_3$, phenyl-$SO_3$ or p-toluyl-$SO_3$. In a preferred embodiment, $X^\ominus$ is $BF_4$, $ClO_4$, $CF_3SO_3$, $PF_6$; particularly preferably $X^\ominus$ is $BF_4$.

Y and Z each are preferably ethylene, or Y and Z together are preferably a diene having 6 to 8 C atoms whose diene groups are bonded in particular via 2 C atoms. In a preferred embodiment Y and Z are each ethylene or Y and Z together are 1,5-cyclooctadiene, norbornadiene or 1,5-hexadiene.

The $C_1$-$C_4$-alkyl substituent can be methyl, ethyl, n-propyl, i-propyl or butyl. Preference is given to methyl.

In a preferred embodiment, $R^1$ and $R^2$ are each phenyl or together —$(CH_2)_4$—.

An alkyl $R^1$ can be linear or branched $C_1$-$C_{12}$ alkyl, preferably $C_1$-$C_6$ alkyl. Examples are methyl, ethyl, n-propyl, i-propyl, n-, i- and t-butyl, n-pentyl, 2-methylbut-1-yl, hexyl, pentyl, octyl, 2-ethylhex-1-yl, nonyl, decyl, undecyl and dodecyl. In a preferred embodiment, alkyl $R^1$ is methyl, ethyl, n- or i-propyl or n-, i- or t-butyl. Cycloalkyl $R^1$ preferably contains 5 or 6 ring C atoms and is preferably cyclopentyl or cyclohexyl. Aryl $R^1$ is preferably $C_6$-$C_{10}$-aryl, preferably phenyl or naphthyl. Aralkyl $R^1$ is preferably $C_7$-$C_{12}$-aralkyl and can be for example benzyl, α- or β-phenylethyl, 2-phenylprop-1-yl, 3-phenylprop-1-yl, 4-phenylbut-1-yl or phenylhexyl Alkaralkyl $R^1$ is preferably $C_8$-$C_{14}$-alkaralkyl and cap be for example methylbenzyl, ethylbenzyl, propylbenzyl, hexylbenzyl or α- or β-(methylphenyl)ethyl.

In a preferred embodiment, $R^1$ is $C_1$-$C_4$-alkyl, cyclopentyl, cyclohexyl, phenyl, benzyl, α-phenylethyl or methylbenzyl. A preferred subgroup of the iridium complexes of the formula I are those in which $X^\ominus$ is $BF_4^\ominus$ and Y and Z together are cyclooctadiene.

The iridium complexes of the formula I can be obtained in a conventional manner [see Inorganica Chimica Acta 73 (1983), pp. 275-279] by reacting [(acetonitrile)$_2$ (YZ)]IrX, in which X, Y and Z are as defined on page 2 with a diamine of the formula II

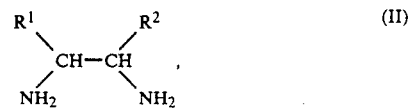

in which $R^1$ and $R^2$ are as defined above. The preparation of the acetonitrile complex is likewise described here. The IrCl(YZ)]$_2$ complexes used for preparing the acetonitrile complex are for example obtainable by reacting dichlorotetrabis(alkene)diiridium(I) (Alkene for example cyclooctene) with ethylene or a diene YZ.

The reactions are generally carried out at temperatures of −10° to 30° C. in an inert solvent and in the absence of air. Suitable inert solvents are for example hydrocarbons such as benzene, toluene, xylene, petroleum ether, hexane, cyclohexane, methylcyclohexane; and ethers, for example diethyl ether, dibutyl ether, tetrahydrofuran and dioxane, as well as halogenated hydrocarbons, for example chloroform, methylene chloride or chlorobenzene. To prepare salts of formula I with anions of monobasic inorganic or organic acids, the salts of the formula I can be reacted with an alkali metal salt $M^\oplus X'^\ominus$ either directly after the reaction or after isolation and purification and renewed solution in polar solvents (for example alcohols, ethers or ketones, in the presence or absence of water), and thereafter be isolated. $X'^\ominus$ is a monobasic or organic acid anion other than $X^\ominus$, $M^\oplus$ is preferably sodium. The iridium complexes according to the invention are crystalline and can be isolated by filtration and purified by recrystallization.

Optically active 1,2-diamines of the formula II are known, in some instances commercially available, or they are preparable in a conventional manner and conventional racemate splitting. (R)-1,2-diaminopropane and (R,R)-1,2-diaminocyclohexane are commercially available. (R,R)-1,2-diamino-1,2-diphenylethane is described in the literature. Optically active 1,2-diamine of the formula II in which $R^2$ is H can be prepared from optically active α-aminocarboxylic acids by the following method ($Z^1$ is —COOCH$_2$C$_6$H$_5$, * signifies predominantly S- or R-configuration):

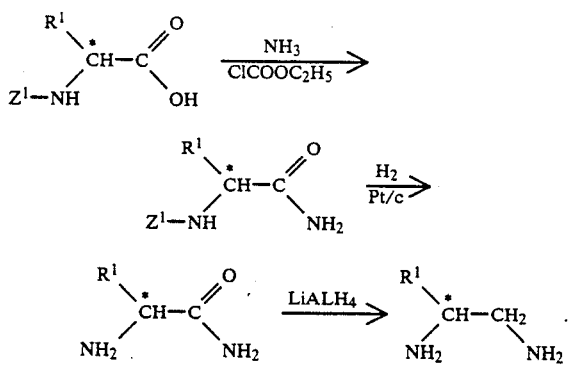

Examples of such diamines are (R)- and (S)-1-methyl-1,2-diaminoethane, (R)- and (S)-1-ethyl-1,2-diaminoethane, (R)- and (S)-1-(n-propyl)-1,2-diaminoethane, (R)- and (S)-1-(ipropyl)-1,2-diaminoethane, (R)- and (S)-1-(n-butyl)-1,2-diaminoethane, (R)- and (S)-1-(i-butyl)-1,2-diaminoethane, (R)- and (S)-1-(t-butyl)-1,2-diaminoethane, (R)- and (S)-1-phenyl-1,2-diaminoethane, (R)- and (S)-1-benzyl-1,2diaminoethane.

The invention further relates to the use of the iridium complexes according to the invention as enantio-selective homogeneous catalysts for the transfer hydrogenation of in particular prochiral ketones with secondary alcohols. A suitable secondary alcohol is in particular isopropanol. The reaction is advantageously carried out at elevated temperature in the absence of oxygen. Advantageously the secondary alcohol used is used as solvent. The catalyst concentration is preferably $10^{-2}$ to $10^{-5}$ mol/l, based on the reaction volume. The reaction is preferably carried out in the presence of a base, in particular NaOH.

The following Examples illustrate the invention in more detail. The determination of the enantiomer excess (ee) is effected in accordance with Mosher [J. Org. Chem. 34, pp. 2543 (1969)].

EXAMPLES 1–6

Under argon protective gas 0.469 g (1.0 mmol) of bis(acetonitrile)(cycloocta-1,5-diene)iridium tetrafluoroborate is dissolved in 15 ml of dichloromethane. At room temperature and with stirring, a solution of 5 ml of dichloromethane and 1.0 mmol of the primary diamines (N,N-ligand) mentioned in table 1 is added dropwise. After 1 hour the reaction mixture is concentrated under about 600 Pa to about one third of the volume. If no spontaneous crystallization of the products takes place, 60 ml of diethyl ether are added, and the product precipitates as a solid precipitate in the course of 3 hours. The product is filtered off with suction under argon, washed three times with diethyl ether and is dried under 0.1 Pa for about 16 hours. The colour and the elemental analysis thereof are listed in table 1.

EXAMPLE 7 Preparation of

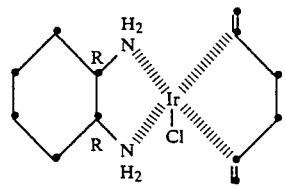

Under argon protective gas, 0.327 g (0.365 mmol) of di-μ-chlorotetrakis(cyclooctene)diiridium(I) is dissolved in 25 ml of benzene. 2.5 ml of 1,5-hexadiene are added at 10° C. After 30 minutes of stirring, 0.8 mmol of (—)R, R-1,2-diaminocyclohexane is added dropwise. After 1 hour's stirring, 60 ml of petroleum ether (60°–80° C.) are added, and the mixture is maintained at 0° C. for 16 hours. The product precipitates in the form of a fine yellow powder. It is washed with petroleum ether (60°–80° C.) and is dried under 0.1 Pa for 16 hours. Colour: yellow Microanalysis (formula C$_{12}$ H$_{24}$ N$_2$ Cl Ir):

|  | C | H | N | Cl |
|---|---|---|---|---|
| Calculated: | 33.99 | 5.71 | 6.61 | 8.36 |
| Found: | 33.4 | 5.9 | 5.7 | 7.4 |

TABLE 1

| Example No. | Complex | N,N (absolute configuration) | Colour | Elemental Analysis (% by weight) |
|---|---|---|---|---|
| 1 | [Ir(N,N)(COD)]BF$_4$ | (R,R) cyclohexane-1,2-diamine H$_2$N, NH$_2$ | yellow | Found: C 32.25; H 5.04; N 5.40; F 15.00<br>Calc.: C 32.37; H 5.43; N 5.39; F 14.63 |
| 2 | " | Ph, Ph (R,R) H$_2$N, NH$_2$ | yellow | Found: C 40.83; H 4.40; N 4.40; Ir 29.6<br>Calc.: C 41.58; H 5.08; N 4.41; Ir 30.2 |
| 3 | " | CH$_3$ (R) H$_2$N, NH$_2$ | lemon yellow | Found: C 28.55; H 4.70; N 6.13; Ir 40.0<br>Calc.: C 28.64; H 4.81; N 6.07; Ir 41.6 |

TABLE 1-continued

| Example No. | Complex | N,N (absolute configuration) | Colour | Elemental Analysis (% by weight) |
|---|---|---|---|---|
| 4 | " | 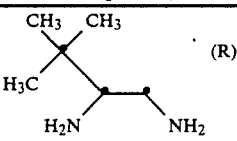 (R) | greenish beige | Found: C 32.20; H 5.46; N 5.36; F 14.84<br>Calc.: C 31.70; H 5.84; N 5.28; F 14.33 |
| 5 | " | 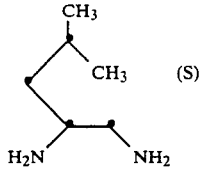 (S) | greenish beige | Found: C 31.62; H 5.46; N 5.21; F 14.42<br>Calc.: C 31.70; H 5.89; N 5.28; F 14.33 |
| 6 | " | 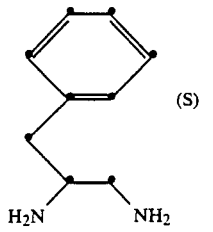 (S) | yellowish beige | Found: C 35.39; H 4.84; N 4.89; Ir 33.4<br>Calc.: C 35.61; H 5.27; N 4.89; Ir 33.52 |

EXAMPLE 8 (USE EXAMPLE)

65.6 mg of a complex prepared as described in example 1 are dissolved in the absence of oxygen (under argon) in 38.5 ml of isopropanol. After 1 hour of stirring at 60° C., 6.16 ml of 0.1N sodium hydroxide solution are added. This is followed by a further hour of stirring at 60° C., and subsequently a solution of 38.5 ml of isopropanol and 2.28 g of butyrophenone is added in the absence of oxygen. The molar ratio substrate:catalyst is thus [substrate]/[catalyst]=100, the catalyst concentration being $2 \times 10^{-3}$ mol/l.

After 4 hours at 60° C., the yield of 1-phenyl-1butanol is found by gas chromatography (OV 101, 120° C. isothermal) to be 91.0%.

To determine the enantiomer content by the method of Mosher, a sample (about 0.5 ml) is substantially freed of solvent and is treated at 0° C. with 50 μl of optically pure α-methoxy-α-trifluoromethylphenylacetyl chloride and 0.25 ml of dry pyridine. After 15 minutes the temperature is raised to 70° C. for 30 minutes, after cooling down 3 ml of 10 percent citric acid solution are added, and the diastereomeric esters are extracted with ether. By gas chromatography (CW 20 capillary column, 190° C. isothermal) an enantiomer excess of (S)-1-phenylbutanol of 44.6% is determined.

What is claimed is:

1. An optically active iridium complex of formula I in which

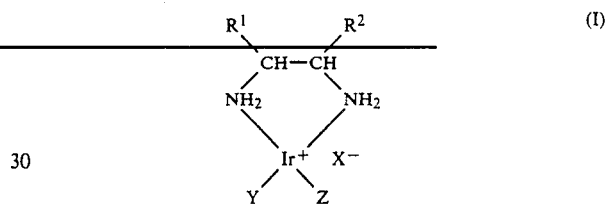

$R^1$ and $R^2$ are each phenyl each of which is attached to a separate carbon atom with an R configuration or together are unsubstituted or $C_1$-$C_4$-alkyl substituted —$(CH_2)_4$— or $R^1$ is linear or branched $C_1$-$C_{12}$-alkyl, $C_5$-$C_6$-cycloalkyl, $C_6$-$C_{10}$-aryl, $C_7$-$C_{12}$-aralkyl or $C_8$-$C_{14}$-alkaralkyl and $R^2$ is H, $X^-$ is $F^-$, $Cl^-$, $Br^-$, $I^-$, $ClO_4^-$, $NO_3^-$, $BrO_3^-$, $HSO_4^-$, $H_2PO_3^-$, $H_2PO_4^-$, $BF_4^-$, $SbF_6^-$, $AsF_6^-$, $SbCl_6^-$, $SbCl_5F^-$, $HCOO^-$, $CH_3COO^-$, $CCl_3COO^-$, $CH_3SO_3^-$, $CCl_3SO_3^-$, $CF_3SO_3^-$, phenyl-$SO_3^-$, p-toluyl-$SO_3^-$, and Y and Z are each ethylene or Y and Z together are an acyclic or cyclic diene having 6 to 10 C atoms wherein the double bonds are separated by 1 or 2 C atoms.

2. An iridium complex of the formula I according to claim 1, in which $X^\ominus$ is $CF_3SO_3^\oplus$, $ClO_4^\oplus$, $BF_4^\oplus$ or $PF_6^\oplus$.

3. An iridium complex of the formula I according to claim 1, in which Y and Z are ethylene or Y and Z together are 1,5-cyclooctadiene, norbornadiene or 1,5-hexadiene.

4. An iridium complex of the formula I according to claim 1, in which $R^1$ and $R^2$ are phenyl or together —$(CH_2)_4$—.

5. An iridium complex of the formula I according to claim 1, in which $R^1$ is linear or branched $C_1$-$C_{12}$-alkyl, cycloalkyl having 5 or 6 ring C atoms, $C_6$-$C_{10}$-aryl, $C_7$-$C_{12}$-aralkyl or $C_8$-$C_{14}$ alkaralkyl and $R^2$ is H.

6. An iridium complex of the formula I according to claim 5, in which $R^1$ is $C_1$-$C_4$-alkyl, cyclopentyl, cyclohexyl, phenyl, benzyl, α-phenylethyl or methylbenzyl.

7. An iridium complex of the formula I according to claim 5, in which alkyl $R^1$ is methyl, ethyl, n-propyl, i-propyl, n-butyl, i-butyl or t-butyl.

8. An iridium complex of the formula I according to claim 1, in which $X^\ominus$ is $BF_4^\ominus$ and Y and Z together are cyclooctadiene.

* * * * *